United States Patent [19]

Kaneko et al.

[11] Patent Number: 4,957,508

[45] Date of Patent: Sep. 18, 1990

[54] MEDICAL TUBES

[75] Inventors: Noriaki Kaneko; Yoshimi Hirata; Masahiro Moriwaki, all of Yokohama, Japan

[73] Assignee: Ube Industries, Ltd., Yamaguchi, Japan

[21] Appl. No.: 114,499

[22] Filed: Oct. 30, 1987

[30] Foreign Application Priority Data

Oct. 31, 1986 [JP] Japan ................ 61-258369

[51] Int. Cl.$^5$ ............................ A61F 2/06; A61F 2/04
[52] U.S. Cl. ............................................ 623/12; 623/1
[58] Field of Search ................ 623/1, 2, 10, 11, 12; 66/172 R

[56] References Cited

U.S. PATENT DOCUMENTS

| | | | |
|---|---|---|---|
| 4,047,252 | 9/1977 | Liebig et al. | 623/1 |
| 4,173,689 | 11/1979 | Lyman et al. | 521/64 |
| 4,623,347 | 11/1986 | Kira | 623/1 |
| 4,704,130 | 11/1987 | Gilding et al. | 623/1 |
| 4,728,328 | 8/1988 | Hughes et al. | 623/1 |

FOREIGN PATENT DOCUMENTS 51-18991 6/1976 Japan.
61-14823 4/1986 Japan.

*Primary Examiner*—David J. Isabella
*Attorney, Agent, or Firm*—Birch, Stewart, Kolasch & Birch

[57] ABSTRACT

A medical tube characterized in that it dilates at its cut ends toward the external surface when it is cut at any random portion transversely relative to its longitudinal direction.

The patency of the sutured portion may be maintained in good condition over a long time, since pannus formation in the internal cavity can be obviated at the sutured portion between an organ of a living body and an artificial medical tube.

4 Claims, 1 Drawing Sheet

MEDICAL TUBES

BACKGROUND OF THE INVENTION

The present invention relates to a medical tube with excellent quality and, more specifically to a medical tube particularly suitable as an artificial blood vessel of medium or small diameter.

It has been conventional to practice blood vessel replacement or perform a bypass operation using an artificial medical tube which is compatible with organic tissues, as described, for example, in U.S. Pat. No. 4,173,689, as a radical operation for securing and achieving the functions of a diseased ureter, trachea, esophagus or blood vessel.

Typical medical tubes include one prepared by knitting or weaving a polyester fiber into the form of a tube, and then crimps are provided thereto as described in Japanese Unexamined Patent Publication No. 94699/1977; or one prepared by forming polyethylene tetrafluoride into the form of a tube, followed by stretching to impart thereto a fibrous microstructure as described in Japanese Unexamined Patent Publication No. 7284/1971, etc.

These medical tubes are still not satisfactory, although relatively good results are obtained when they are applied as an artificial ureter, trachea, esophagus or blood vessel having an inner diameter of 10 mm or more. In artificial blood vessels having small inner diameters of 7 mm or less, particularly 6 mm or less, patency results are extremely poor, and a tube obtained from polyethylene tetrafluoride by imparting porosity to the tube has only been used for limited purposes.

Clinicians earnestly desire completion of an artificial blood vessel which is applicable as a peripheral artery having an inner diameter of 3 to 4 mm, since it can be used widely for such purpose as a bypassing vehicle in coronary artery operations. While various studies are being made recently on medium and small diameter blood vessels, no such vessels are currently available.

With the above artificial blood vessel obtained by knitting or weaving a polyester fiber, a thrombotic layer of as thick as 1 mm may be formed in the internal cavity thereof. Accordingly, if this material is used as a medium or small diameter blood vessel, its internal cavity or channel will soon become obstructed by the formation of thrombi.

Thus, it is a prerequisite for the material itself to have a sufficient antithrombotic property and is not obturated by the initial thrombi formation.

A number of artificial blood vessels having different end faces and internal surface structures were made for testing purposes using several kinds of polyether polyurethanes or polyurethane ureas having different antithrombotic properties. As a result of implantation experiments with dogs using the above artificial blood vessels, it has been found that the obturation can be entirely attributed to the panni at the sutured portion.

The expression, pannus (panni), used herein means a granulation which has grown from the cut end of an organ wall of a living body at a portion where the organ of a living body has been cut and anastomically connected with a medical tube growth of the panni toward the internal cavity causes turbulence in the flow of blood and the like which passes therethrough. Particularly in artificial blood vessels, if pannus grows in that portion where the blood flow is transferred from the organic blood vessel to the artificial blood vessel, namely at the center side of the sutured portion, blood stagnation is created immediately after the formation of the pannus, and accumulating thrombi gradually becomes organized and enlarged. As a result, the effective sectional area of the internal cavity, as well as blood flow rate, may decrease, and finally the inside of the artificial blood vessel will become completely obturated with thrombi.

This formation of pannus is due to the self-recovering function of the cut tissue, while which is essentially unavoidable, the growth of which is particularly remarkable when the section is contacted with a foreign body. Accordingly, if the anastomosis or connection of an organ of a living body with an artificial medical tube is achieved without contacting the sections thereof with each other, growth of panni can be inhibited.

The artificial medical tube of the present invention which dilates at the cut ends toward its external surface can be sutured with an organ of a living body without its cut ends being in contact with each other. This inhibits growth of panni and exhibits excellent patency.

Also, medical tubes have been provided which have been formed to have a predetermined length preliminarily with both ends being dilated toward the external surface thereof. However, since such medical tubes are required in a variety of lengths depending on the patients needs, it is not practically possible to have tubes always in hand over a wide variety of lengths.

SUMMARY OF THE INVENTION

The medical tube according to the present invention is characterized in that the cut end surfaces dilate toward the external surface thereof when it is cut transversely relative to its longitudinal direction at any optional positions.

Namely, the medical tube according to the present invention is a novel medical tube in which the cut ends and the proximate portions thereof dilate toward its external surface upon cutting, when it is cut into a necessary length according to the need in each case.

BRIEF DESCRIPTION OF THE DRAWING

The present invention will become more fully understood from the detailed description given hereinbelow and the accompanying drawings which are given by way of illustration only, and thus, are not limitative of the present invention, and wherein.

DESCRIPTION OF THE PREFERRED EMBODIMENTS

Figure 1:
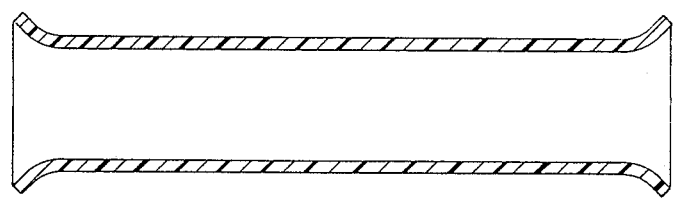
FIG. 1 is an embodiment of the medical tube of the present invention shown in cross-section along the longitudinal axis thereof.

The high molecular compound to be used according to this invention is a substance which has excellent compatibility with blood and tissues, i.e. a polymer which is devoid of acute or chronic toxicity, heat built-up or hemolyticity, and induces no inflammation in the surrounding tissues when it is implanted over a long period of time. Such polymers include, for example, polyvinyl halide, polystyrene and its derivative, polyolefin series polymers, polyester series condensates, cellulose series high polymers, polyurethane series high polymers, polysulfone series resins, polyamide series high polymers, etc. Of course, copolymers or mixtures of the above listed compounds may also be used. Because of their dynamic property and stability in a living body, as well as antithrombotic property, the preferred polymers are polyurethane series compounds. Such compounds typically include polyurethane, polyurethane urea, mixtures of these with a silicone polymer and compounds having a structure of reciprocally penetrative reticulation. These compounds also include segmented polyurethanes or polyurethane urea, a compound containing polydimethylsiloxane in its backbone and those containing fluoride in the hard and soft segments. A polyether type polyurethane or polyurethane urea is preferred to a polyester type polyurethane in that it is hardly subject to biodegradation.

As to the above polyethers constituting the polyether segment of the polyurethane, although polytetramethylene oxide is most preferred, other polyalkylene oxides may also be used, preferably provided that the alkylene has 2 and/or 3 carbon atoms. Typical examples of such polyalkylene oxides include polyethylene oxides, polypropylene oxides, ethylene oxide-propylene oxide copolymers and block copolymers. There may also be used polyurethanes containing a polytetramethylene oxide segment and a polyalkylene oxide (provided that the alkylene has 2 and/or 3 carbon atoms) in the same backbone and provided with the hydrophilicity and dynamic property.

The polyether forming the soft segment has a molecular weight in the range of usually 400 to 3,000, preferably 450 to 2,500, more preferably 500 to 2,500. The most excellent polyether segment of all has a molecular weight of 800 to 2,500, which is particularly a polytetramethylene oxide chain having a molecular weight of 1,300 to 2,000. If the molecular weight of this polyether soft segment exceeds 3,000, the mechanical property of the resulting polyurethane medical tube may be very poor; and if it is less than 400, it is too hard to be used as a medical tube, if formed.

The synthesis of polyurethane may be carried out by use of a conventional method comprising allowing the above polyether terminated with hydroxyl groups at its both ends to react with a known diisocyanate used for the synthesis of the polyurethane, including 4,4'-diphenylmethane diisocyanate, toluidine diisocyanate, 4,4'-dicyclohexylmethane diisocyanate, hexamethylene diisocyanate, etc. to produce an isocyanate-terminated prepolymer, and subjecting the resulting product to chain extension with the use of a diamine such as ethylene diamine, propylene diamine and tetramethylene diamine or a diol such as ethylene glycol, propylene glycol and butanediol.

The medical tube of the present invention can be prepared, for example, in the following manner.

A porous medical tube can be obtained by a process comprising thrusting forward a core rod having a round cross-section and made of a rigid body from a circular orifice to extrude a solution of a high molecular weight compound from a gap slit defined between said orifice and said core rod in such a manner that the solution is spread over the whole surface of the core rod. The core rod is introduced into a solidifying medium to solidify said high molecular compound around said core rod, followed by washing well with water and desolvation and then removing out the core rod.

The solution used for the process may preferably be made to have a viscosity of 0.5 poise or more at the molding temperature. The viscosity of less than 0.5 poise may cause uneven wall thickness in the course of the molding process. Advantageously, there may be less limitation to the molding process at a viscosity of 10 poises or more.

On the other hand, there is almost no limitation in the higher side of the viscosity, and the molding can be sufficiently achieved even with a solution of less fluidity. The molding can readily be carried out even with the use of a solution of about 5,000 poises at which the molding could hardly be carried out according to a hollow fiber production process employing a conventional annular nozzle. However, since it is desired from the viewpoint of production to relatively simply achieve the deaeration of a solution, the solution may preferably have the viscosity of 3,000 poises or less, more preferably 2,000 poises or less.

The solvent used for the solution of the high molecular weight compounds can be selected from known solvents appropriately corresponding to the respective substances to be used. However, a water-soluble solvent is advantageous in order to prevent the solvent remaining in a product and from a viewpoint of saving the cost in the production steps. Such a solvent may include, for example, dimethylformamide, dimethylacetamide, dimethylsulfoxide, N-methyl-2-pyrrolidone, dioxane, tetrahydrofuran, acetone, etc. In the production process of the present invention, the solution does not necessarily have to be in a good solubilized state. For this reason, a poor solvent or a swelling agent such as urea may be mixed and used in a large amount. This is very advantageous in the production of the medical tube of the present invention. Namely, the solvent system can be selected in a wide range, whereby the porosity (the degree of being porous) can be varied widely with ease and without any particular complicated steps such as the step of using a pore-forming agent.

The rod comprising a rigid body used as the core may be made of a substance that does not dissolve in the solution and does not readily change its shape while it is led into the solidifying medium. As a corrosion resistance property is also required, particularly preferred are materials applied with chrome plating or Teflon processing on stainless steel, steel, brass, etc.

The core rod thrust forward in such a state that the solution is spread over the entire peripheral surface is directly, or after passing through a certain dry section, led into a solidifying medium.

Specifically, there can be used either a wet solidification system according to which the high molecular compound solution discharged from the gap slit defined between the circular orifice and the core rod is directly fed into a water system solidifying medium, or a dry and wet solidification wherein the same is led into the water system solidifying medium via a dry section.

The thus obtained medical tube is dried at a temperature range of room temperature to 60° C. for more than several hours and then reversed such that the internal cavity surface may appear as the external surface. The medical tube obtained dilates toward its external surface at the both ends and when it is cut at any random position, new cut ends likewise dilate toward the external surface. This is because a dilating force acts on the internal surface and a shrinking force acts on the external surface by reversing the tube.

This invention will be described below in greater detail by way of Examples. The "%" shown in the following example refers to "% by weight".

EXAMPLE 1

Polytetramethylene glycol terminated with hydroxyl groups at its both ends and having a molecular weight of 1,300 was reacted with 4,4'-diphenylmethane diisocyanate to give a both ends an isocyanate-terminated prepolymer, which was subjected to chain extension with the use of butanediol to synthesize polyurethane. The polyurethane thus synthesized was purified by repeating reprecipitation three times in a tetrahydrofuran/ethanol system solvent. The purified polyurethane was dissolved in dimethylacetamide to give a 20% solution.

From a circular orifice of 6 mm in diameter, a stainless steel rod of 4 mm in outer diameter disposed concentric with the above orifice was thrust forward at a constant speed. The above polyurethane solution was extruded from the uniform annular gap between the stainless steel rod thus thrust forward and the orifice so that the solution was spread over the whole peripheral surface of the rod. The rod was then introduced into water maintained at 25° C., and the solution was solidified from the outside. The solidified product was kept immersed in the water for 48 hours to sufficiently remove the solvent.

This rod was taken out and the resulting porous medical tube was reversed from one end such that the internal cavity surface appeared as the exterior surface, followed by drying at 40° C. for 24 hours.

The thus obtained tube had an inner diameter of 3.7 mm and an outer diameter of 5.0 mm, and its both ends dilated toward its exterior surface continuously as shown in FIGURE. This tube had an inclination to dilate toward its exterior surface always when it is cut at any random position. Cutting test of this tube demonstrated that the dilation of the cut end portions occurred in the range of 2 to 3 mm from the ends and had a dilated maximum inner diameter in the range of 4.2 to 4.7 mm.

The medical tube was sterilized with ethylene oxide gas at room temperature to be used as an artificial blood vessel. The abdominal artery of six hybrid adult dogs each having a body weight of 7 to 9 kg was resected over a length of 5 cm. The above medical tube was implanted in this resected portion by means of end-to-end suturing using a 6-0 nylon thread. By virtue of the dilation of the cut ends of the artificial blood vessel toward its external surface, anastomosis could very readily be carried out such that the internal surface of the blood vessel of the living body is contacted with the internal surface of the artificial blood vessel.

Upon examination, all the artificial blood vessels implanted in the six dogs were still functioning well twelve months after implantation. No constriction of the sutured portion due to the formation of pannus was observed in any case through angiography, one, two, three, five, nine and twelve months after implantation.

EXAMPLE 2

Polytetramethylene glycol terminated with hydroxyl groups at both of its ends and having a molecular weight of 1,890 was reacted with 4,4'-dicyclohexylmethane diisocyanate to give an isocyanate-end terminated prepolymer according to a conventional method the prepolymer was subjected to chain extension with the use of ethylene diamine to synthesize polyurethane urea. The polyurethane urea thus synthesized was purified by repeating reprecipitation three times in a dimethylformamide/ethanol system solvent. The purified polyurethane urea was dissolved in dimethylformamide to give a 20% solution.

From a circular orifice of 7.2 mm in diameter, a stainless steel rod of 5 mm in outer diameter having been set to be concentric with this orifice was thrust forward at a constant speed, and the above polyurethane urea solution was extruded from the uniform annular gap between the stainless steel rod thus thrust forward and the orifice such that the solution spread over the whole peripheral surface of the rod, which rod was then introduced into water maintained at 20° C. The solidification of the extruded polyurethane urea tube was effected from the outside, i.e. from the external surface slowly to form a white polyurethane urea film around the peripheral surface of the stainless steel rod after about 30 minutes. The thus obtained film was left to stand for about 24 hours to effect complete solidification, followed by immersing in flowing water for 20 hours to completely remove dimethylformamide. The thus obtained polyurethane urea tube was peeled off from the stainless steel rod and reversed such that the internal cavity surface may appear as the external surface, followed by drying at 35° C. for 24 hours.

The tube obtained dilated at the both ends toward its exterior surface as described in Example 1 and had an inclination to dilate toward its exterior surface at the cut ends when it is cut at any random position.

This medical tube was used as an artificial blood vessel and implanted into three hybrid adult dogs each having a body weight of 6.5 to 7 kg in the same manner as described in Example 1. Upon angiography of the implanted tube no formation of pannus was observed one, three and five months after implantation.

COMPARATIVE EXAMPLE

Using the same polyurethane solution as used in Example 1, a medical tube was formed and the solvent was removed. The thus obtained tube was used as an artificial blood vessel as such without reversing it. This artificial blood vessel was even in diameter both at the cut ends and at the middle portion. This tube also showed no change in diameter of its cut ends even when it is cut at any random portion.

This artificial blood vessel was implanted in four adult dogs in the same manner as described in Example 1. As a result, obturation occurred around the sutured portion one month after implantation in one case; and in the other three cases, notable formation of pannus was observed at the sutured portions by angiography two months after implantation. One dog of the latter three cases was sacrificed for observation to find that a pannus with a thickness of about 2 mm has grown and a large amount of organized thrombi were deposited immediately downstream thereof. Complete obturation occurred around the sutured portion also in the other two dogs six months after implantation.

According to the present invention, appearance of the sutured portion is maintained in good condition over a long time, since pannus formation in the internal cavity is obviated at the sutured portion between an organ of a living body and an artificial medical tube. The medical tube according to the present invention is applicable as an artificial ureter, artificial trachea, artificial esophagus and artificial blood vessel, especially as a small or medium diameter blood vessel having an inner diameter of 7 mm or less.

We claim:

1. An implantable tubular synthetic prosthesis for repairing or replacing tubular vessels which comprises a porous, high molecular weight elastomeric tube made of an elastomer selected from the group consisting of polyurethane, polyurethane urea, mixtures of polyurethane and polyurethane urea and mixtures of polyurethane and polyurethane urea with a silicone polymer, said elastomeric tube having an internal and external surface, wherein the internal surface exhibits a dilating force and the external surface exhibits a shrinking force such that the end portions of the tube dilates outwardly towards the external surface of the tube and said tube further dilating along its cut end portions to the external surface thereof when it is cut at any random position along the tube, transverse to its longitudinal direction, said dilation occurring in the area within 5 mm from said ends and cut ends, respectively, and the dilated maximum inner diameter is 1.4 times the inner diameter thereof.

2. The tubular synthetic prosthesis of claim 1 having an inside diameter of 7 mm or less.

3. The tubular synthetic prosthesis of claim 1 having an inside diameter of 3–4 mm.

4. The tubular synthetic prosthesis of claim 1 wherein the elastomer has a molecular weight of 400 to 3,000.

* * * * *